United States Patent [19]

Takács et al.

[11] 4,365,064
[45] Dec. 21, 1982

[54] 1,2,4-OXADIAZOLIN-5-ONE DERIVATIVES, PROCESS FOR THEIR PREPARATION AND PHARMACEUTICAL COMPOSITIONS CONTAINING THEM

[75] Inventors: Kálmán Takács; Ilona Kiss née Ajzert; Antal Simay; Péter Literáti Nagy; Mária Hetyey née Papp; Marian Ecsery née Puskás, all of Budapest; Laszló Szekeres; Gyula Papp, both of Szeged; Sándor Virágh, Budapest; Evá Udvardy, Szeged, all of Hungary

[73] Assignee: Chinoin Gyogyszer es Vegyeszeti Termekek Gyara Rt, Budapest, Hungary

[21] Appl. No.: 196,583

[22] Filed: Oct. 14, 1980

[30] Foreign Application Priority Data

Oct. 11, 1979 [HU] Hungary .................. CI 1973

[51] Int. Cl.³ .................. C07D 413/06; A61K 31/47
[52] U.S. Cl. .................. 546/148; 424/258
[58] Field of Search .................. 546/148

[56] References Cited

U.S. PATENT DOCUMENTS

3,994,891 11/1976 Hughes et al. .................. 546/148
4,038,279 7/1977 Renth et al. .................. 544/363
4,187,220 2/1980 Takacs et al. .................. 546/145

FOREIGN PATENT DOCUMENTS

6365M 4/1967 France .................. 424/250
6988M 3/1968 France .................. 424/250

OTHER PUBLICATIONS

Tackas, K., et al., Chemische Berichte, 108, pp. 1911–1923, 1975.
Papp et al., Arch. Int. Pharmacodyn, 1966, 160, No. 1.
Burger, A., "Medicinal Chemistry", 1960, p. 497.
Archives Internationales Pharmacodynamie et de Therapie (1966) vol. 160, pp. 146–158.

*Primary Examiner*—Donald G. Daus
*Assistant Examiner*—Sharon A. Gibson
*Attorney, Agent, or Firm*—Karl F. Ross

[57] ABSTRACT

The invention concerns new compounds of the formula (I)

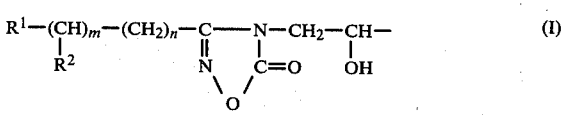

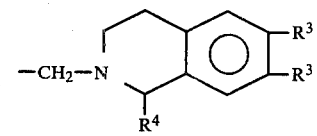

wherein
$R^1$ is hydrogen, phenyl or phenyl substituted with at least one alkyl having 1 to 4 carbon atoms, halogen, alkoxy having 1 to 4 carbon atoms or nitro;
$R^2$ is alkyl having 1 to 4 carbon atoms, cycloalkyl having 5 to 7 carbon atoms, phenyl, or phenyl substituted with at least one alkyl having 1 to 4 carbon atoms, halogen, alkoxy having 1 to 4 carbon atoms or nitro;
$R^3$ is alkoxy having 1 to 4 carbon atoms or hydrogen,
$R^4$ is hydrogen, alkyl having 1 to 4 carbon atoms unsubstituted or substituted with alkoxy having 1 to 4 carbon atoms, benzyloxy or cyano, phenyl, or phenyl substituted with at least one alkyl having 1 to 4 carbon atoms, halogen, alkoxy having 1 to 4 carbon atoms or nitro, or phenyl-($C_{1-4}$alkyl)-alkyl, in which the phenyl moiety may bear an alkoxy substituent having 1 to 4 carbon atoms or a halogen;

m and n are each 0, 1 or 2 or a pharmaceutically acceptable acid addition or quaternary salt thereof.

The compounds are potent vasodilators and exert a favorable influence on the extremital blood flow. They also show a heart function influencing activity.

Methods for the preparation of said compounds and pharmaceutical compositions containing them are also the subject of the invention.

3 Claims, No Drawings

1,2,4-OXADIAZOLIN-5-ONE DERIVATIVES, PROCESS FOR THEIR PREPARATION AND PHARMACEUTICAL COMPOSITIONS CONTAINING THEM

This invention concerns 1,2,4-oxadiazolin-5-one derivatives, a process for the preparation thereof and pharmaceutical compositions containing them.

More particularly, the invention relates to new 3,4-substituted 1,2,4-oxadiazolin-5-one derivatives of the formula (I)

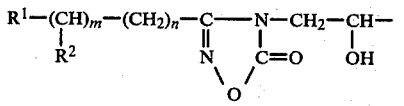

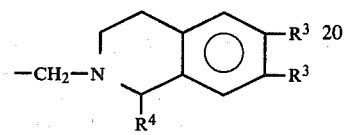

wherein
- $R^1$ is hydrogen, phenyl or phenyl substituted with at least one alkyl having 1 to 4 carbon atoms, halogen, alkoxy having 1 to 4 carbon atoms or nitro;
- $R^2$ is alkyl having 1 to 4 carbon atoms, cycloalkyl having 5 to 7 carbon atoms, phenyl, or phenyl substituted with at least one alkyl having 1 to 4 carbon atoms, halogen, alkoxy having 1 to 4 carbon atoms or nitro;
- $R^3$ is alkoxy having 1 to 4 carbon atoms or hydrogen;
- $R^4$ is hydrogen, alkyl having 1 to 4 carbon atoms, unsubstituted or substituted with alkoxy having 1 to 4 carbon atoms, benzyloxy or cyano, phenyl, or phenyl substituted with at least one alkyl having 1 to 4 carbon atoms, halogen, alkoxy having 1 to 4 carbon atoms or nitro, or phenyl-($C_{1-4}$alkyl), in which the phenyl moiety may bear an alkoxy substituent having 1 to 4 carbon atoms or a halogen;

m and n are each 0, 1 or 2.

The term "alkyl" alone or in alkyl-containing groups covers straight or branched chained hydrocarbon groups.

"X" thoughout the specification is a halogen atom.

According to the invention compounds of the formula (I)—$R^1$, $R^2$, $R^3$, $R^4$, m and n are as hereinabove defined—can be prepared by (a) reacting compounds of the formula (II)

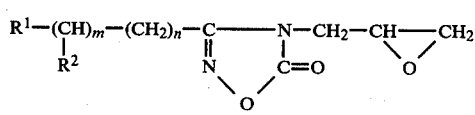

with compounds of the formula (III)

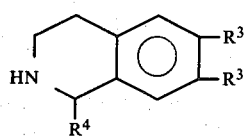

or (b) reacting compounds of the formula (IV)

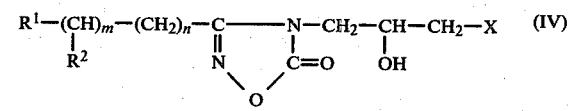

with compounds of the formula (III), or (c) reacting compounds of the formula (V)

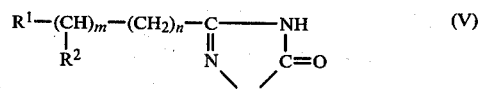

with compounds of the formula (VI)

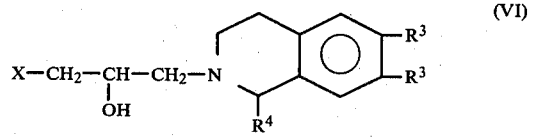

The salts of the compounds of the formula (I) are also within the scope of the invention.

It has been found that the compounds of the formula (I) are potent peripheral vasodilators, and exert a very favorable influence on the extremital blood flow. They also showing a favorable effect on the heart function, more particularly show an excellent antianginal and a considerable antiarrhythmic activity.

Analogous 1,2,4-oxadiazolin-5-one compounds, substituted by a basic side-chain in the 4-position, which does not contain a hydroxyl substituent are disclosed in the French Pat. Nos. M 6988 and M 6365 as coronary vasodilators.

Process variant (a) is preferably carried out in an organic solvent, for example in an alcohol, aromatic hydrocarbon, ether, etc., at a temperature of $-10°$ C. to $+100°$ C.

Compounds of the formula (I) are isolated from the reaction mixture by evaporation or crystallization, and if desired, are converted into the corresponding salts by mineral or organic acids. The bases of the formula (I) can be set free from the corresponding salts by conventional methods. If desired, quaternary salts of the compounds of the formula (I) can also be prepared by alkyl halides or sulfates.

Starting compounds of the formula (II) can be prepared from the corresponding 4-(3-halogen-2-hydroxypropyl)-1,2,4-oxadiazolin-5-one derivatives by basic reactants in a manner known per se [Chem. Ber. 108, 1911 (1975)].

Process variant (b) according to the invention is performed in the presence of bases, for example sodium or potassium hydroxide or alkali carbonates or hydrocarbonates. The reaction is preferably carried out in an organic solvent, preferably in an aqueous organic solvent, at a temperature between 0° C. and 120° C. According to a preferred embodiment, to an alcoholic solution of the reactants an equivalent amount of alkali hydroxide is added, at boiling temperature. Compounds of the formula (III) can be prepared by a similar process as compounds of the formula (II).

Process variant (c) according to the invention is preferably carried out in an organic solvent, in the presence of bases, preferably alkali hydroxides or alcoholates, at a temperature of 0° to 120° C. The product is separated by known techniques, for example by crystallization, extraction, evaporation, etc. If desired, the product can be converted into the corresponding salt by mineral or organic acids; or the bases can be obtained from the corresponding salts by conventional methods.

The new compounds of the formula (VI) can be prepared from the corresponding 1,2,3,4-tetrahydro-isoquinolines by epichlorohydrin, in a manner known per se.

The invention also concerns pharmaceutical compositions containing compounds of the formula (I) as active ingredients. The pharmaceutical compositions are prepared by admixing compounds of the formula (I) or pharmaceutically acceptable salts thereof with non-toxic pharmaceutically acceptable, organic and/or inorganic carriers and optionally other additives. The pharmaceutical compositions can be finished as solid formulations, e.g. tablets, dragées, etc., or liquid formulations, e.g. solutions or emulsions. The pharmaceutical compositions are prepared by known techniques of the pharmaceutical industry.

The active ingredient content of the pharmaceutical compositions can be varied within a wide range, and preferably is between 0.005 and 90%.

The daily dose depends on numerous factors, including the severity of the condition of the patient, the age, weight of the patient, on the formulation employed and the activity of the active ingredient. The daily dose generally is 1 to 500 mg. of active ingredient by kg. of body weight. The above data are for orientation only and deviations, depending on the prescriptions of the physician, in both directions are allowed.

Further details of our invention are to be found in the following Examples, which are not intended to limit the invention in any way.

EXAMPLE 1

To a solution of 2.18 g. of 3-phenyl-4-(2,3-epoxy-propyl)-$\Delta^2$-1,2,4-oxazolidin-5-one in 50 ml. of absolute ethanol 1.33 g. of 1,2,3,4-tetrahydro-isoquinoline are added, and the reaction mixture is refluxed for two hours. The solvent is evaporated and the residue is dissolved in isopropanol. The solution acidified with hydrochloric acid in ethyl acetate to yield 2.47 g. of crystalline 3-phenyl-4-[3-(1,2,3,4-tetrahydro-2-isoquinolyl)-2-hydroxypropyl]-$\Delta^2$-1,2,4-oxadiazolin-5-one hydrochloride are obtained, melting at 210° to 212° C.

Analysis for $C_{20}H_{22}ClN_3O_3$: calculated: C=61.93%; H=5,72% N=10.83%; found: C=61.62%; H=5.50% N=11.06%.

EXAMPLE 2

To a solution of 30.6 g. of 3-phenyl-4-(3-chloro-2-hydroxypropyl)-$\Delta^2$-1,2,4-oxadiazolin-5-one [Chem. Ber. 108. 1911 (1975)] and 15.98 g. of 1,2,3,4-tetrahydro-isoquinoline in 240 ml. of hot absolute ethanol 43.2 ml of a 10% sodium hydroxide solution are added dropwise, in one hour. The reaction mixture is boiled for an additional one hour, whereupon the solvent is evaporated in vacuo. To the residue water is added and it is extracted with two 100 ml. portions of benzene. The benzene solution is dried over sodium sulfate and the solvent is evaporated in vacuo. The residue is dissolved in 100 ml. of methanol and the solution is acidified by introducing hydrogen chloride 30.7 g. of 3-phenyl-4-[3-(1,2,3,4-tetrahydro-2-isoquinolyl)-2-hydroxypropyl]-$\Delta^2$-1,2,4-oxadiazolin-5-one hydrochloride are obtained having the same properties as the product of Example 1.

EXAMPLE 3

To a solution of 5.1 g. of 3-phenyl-4-(3-chloro-2-hydroxypropyl)-$\Delta^2$-1,2,4-oxadiazolin-5-one and 4.0 g. of 6,7-dimethoxy-1,2,3,4-tetrahydro-isoquinoline in 30 ml. of hot absolute ethanol 7.5 ml. of a 10% sodium hydroxide solution are added dropwise, in one hour. The reaction mixture is boiled for an additional one hour, cooled and diluted with water. 6.3 g. of 3-phenyl-4-[3-(6,7-dimethoxy-1,2,3,4-tetrahydro-2-isoquinolyl)-2-hydroxypropyl]-$\Delta^2$-1,2,4-oxadiazolin-5-one are obtained, melting at 159° to 161° C. after recrystallization from absolute ethanol.

Analysis for $C_{22}H_{25}N_3O_5$: calculated: C=64.22%; H=6.12%; N=10.21%; found: C=64.57%; H=6.41%; N=9.90%.

The hydrochloride of the product is precipitated from a methanolic solution by adding hydrochloric acid in methanol. The hydrochloride melts at 210° to 213° C.

Analysis for $C_{22}H_{26}ClN_3O_5$: Calculated: Cl=7.92%; found: Cl=7.88%.

EXAMPLE 4

To 2.18 g. of 3-phenyl-4-(2,3-epoxypropyl)-$\Delta^2$-1,2,4-oxadiazolin-5-one 20 ml. of absolute ethanol and 2.0 g. of 6,7-dimethoxy-1,2,3,4-tetrahydro-isoquinoline are added and the reaction mixture is refluxed for one hour. Upon cooling the mixture is diluted with water. 3.4 g. of 3-phenyl-4-[3-(6,7-dimethoxy-1,2,3,4-tetrahydro-2-isoquinolyl)-2-hydroxypropyl]-$\Delta^2$-1,2,4-oxadiazolin-5-one are obtained having the same properties as the product of Example 3.

The effect of this compound on the cardiovascular system was tested on anaesthetized (Nembutal, 25 mg./kg., i.v.) dogs weighing 10 to 20 kg. The thorax of the dogs was opened and the animals were subjected to artificial respiration. The cardiac output and the blood flow of the carotis artery and femoral artery were determined by "Nycotron 376" electromagnetic rheometer, on the aorta, carotis artery and femoral artery. The results obtained are shown in the following table.

| Dose (mg/kg) i.v. | n number of animals | Deviation of the peripheral circulation from the basic value (%) | Duration of activity (min.) |
| --- | --- | --- | --- |
| 1.0 | 4 | +78 | 9 |
| 2.0 | 3 | +84 | 14 |
| 4.0 | 3 | +90 | 14 |

By employing the doses indicated in the table above the peripheral resistance is reduced by 40, 63 and 69%, respectively. The arterial blood pressure of anaesthetized dogs is decreased by 19% upon administration of a 1 mg/kg. dose of this compound.

On glanduitrine induced model angina [Arch. int. Pharmacodyn. 160, 147 (1966)] on rats the compound administered intravenously possessed the same antianginal effect as Papaverine.

Administration of a 1 mg/kg. i.v. dose of the compound resulted in a 10% increase in the cardiac output, 39% increase in the coronary blood flow and 28% decrease in the coronary resistance of anaesthetized dogs.

EXAMPLE 5

Following the procedure described in Example 4 but starting from 3-phenyl-4-(2,3-epoxypropyl)-$\Delta^2$-1,2,4-oxadiazolin-5-one and 1-methyl-6-7-dimethoxy-1,2,3,4-tetrahydro-isoquinoline, 3-phenyl-4-[3-(1-methyl-6,7-dimethoxy-1,2,3,4-tetrahydro-2-isoquinolyl)-hydroxypropyl]-$\Delta^2$-1,2,4-oxadiazolin-5-one is obtained. The compound is then coverted into its hydrogen maleate hemihydrate by maleic acid in butanol saturated with water. The crystalline salt melts at 156° C.

Analysis for $C_{27}H_{31}N_3O_9.0.5\ H_2O$: calculated: C=58.90%; H=5.86%; N=7.63%; found: C=59.00%; H=6.09%; N=7.28%.

EXAMPLE 6

Following the procedure described in Example 2 but starting from 3-phenyl-4-(3-chloro-2-hydroxypropyl)-$\Delta^2$-1,2,4-oxadiazolin-5-one and 1-cyanomethyl-6,7-dimethoxy-1,2,3,4-tetrahydro-isoquinoline, 3-phenyl-4-[3-(1-cyanomethyl-6,7-dimethoxy-1,2,3,4-tetrahydro-2-isoquinolyl)-2-hydroxypropyl]-$\Delta^2$-1,2,4-oxadiazolin-5-one hydrochloride monohydrate is obtained, melting at 193° to 197° C. after recrystallization from 80% ethanol.

Analysis for $C_{24}H_{27}N_4O_5Cl.H_2O$: calculated: C=57.08%; H=5.79%; N=11.10% Cl=7.02%; found: C=57.33%; H=5.32%; N=11.10%; Cl=7.23%.

EXAMPLE 7

Following the procedure described in Example 2 but starting from 3-phenyl-4-(2,3-epoxypropyl)-$\Delta^2$-1,2,4-oxadiazolin-5-one and 1,2,3,4-tetrahydro-papaverine, 3-phenyl-4-{3-[1-(3,4-dimethoxy-benzyl)-6,7-dimethoxy-1,2,3,4-tetrahydro-2-isoquinolyl]-2-hydroxypropyl}-$\Delta^2$-1,2,4-oxadiazolin-5-one hydrochloride is obtained, melting at 218° to 220° C. after recrystallization from 96% ethanol.

Analysis for $C_{31}H_{36}ClN_3O_7$: calculated: C=62.25%; H=6.07%; N=7.03%; Cl=5.93%; found: C=61.98%; H=6.30%; N=6.77%; Cl=5.83%.

The antiarrhythmic activity of the compound was tested on anaesthetized cats by measuring the fibrillation threshold.

|  | Fibrillation threshold | |
|---|---|---|
|  | auricle $ED_{25}$ (mg/kg.) | ventricle $ED_{25}$ (mg/kg) |
| lidocaine | 3.10 | 5.10 |
| quinidine | 2.60 | 2.60 |
| H-214 | 2.60 | 3.00 |

From the above results it can be clearly seen that the test compound is more effective than lidocain and has about the same activity as quinidine. Similar results were obtained under in vivo conditions.

EXAMPLE 8

Following the procedure of Example 2 but starting from 3-(4-chlorophenyl)-4-(3-chloro-2-hydroxypropyl)-$\Delta^2$-1,2,4-oxadiazolin-5-one and 1,2,3,4-tetrahydro-isoquinoline, 3-(4-chlorophenyl)-4-[3-(1,2,3,4-tetrahydro-2-isoquinolyl)-2-hydroxypropyl]-$\Delta^2$-1,2,4-oxadiazolin-5-one hydrochloride is obtained, melting at 219° to 221° C. after recrystallization from isopropanol.

Analysis for $C_{20}H_{21}Cl_2N_3O_3$: calculated: C=56.88%; H=5.01%; N=9.95%; Cl=16.79%; found: C=56.65%; H=4.86%; N=10.20%; Cl=16.68%.

EXAMPLE 9

Following the procedure described in Example 2 but starting from 3-benzyl-4-(3-chloro-2-hydroxypropyl)-$\Delta^2$-1,2,4-oxadiazolin-5-one and 1,2,3,4-tetrahydro-isoquinoline, 3-benzyl-4[3-(1,2,3,4-tetrahydro-2-isoquinolyl)-2-hydroxypropyl]-$\Delta^2$-1,2,4-oxadiazolin-5-one hydrochloride is obtained, melting at 194° to 197° C. after recrystallization from 96% ethanol.

Analysis for $C_{21}H_{24}ClN_3O_3$: calculated: C=62.76%; H=6.02%; N=10.46%; Cl=8.82%; found: C=63.18%; H=6.13%; N=10.18%; Cl=8.75%.

EXAMPLE 10

Following the procedure described in Example 2 but starting from 3-(3,4-dimethoxybenzyl)-4-(3-chloro-2-hydroxypropyl)-$\Delta^2$-1,2,4-oxadiazolin-5-one and 1,2,3,4-tetrahydro-isoquinoline, 3-(3,4-dimethoxybenzyl)-4-[3-(1,2,3,4-tetrahydro-2-isoquinolyl)-2-hydroxypropyl]-$\Delta^2$-1,2,4-oxadiazolin-5-one hydrochloride is obtained melting at 181° C., after recrystallization from 96% ethanol.

Analysis for $C_{23}H_{28}ClN_3O_5$: calculated: C=59.80%; H=6.11%; N=9.10%; Cl=7.68%; found: C=60.01%; H=6.20%; N=8.79%; Cl=7.90%.

The total peripheral resistance of anaesthetized dogs is decreased by 41% by a 1 mg/kg. i.v. dose of the compound. By administration of a 2 mg/kg. i.v. dose of this compound, a 53.9% inhibition of the T-wave increase induced by glanduitrine can be achieved. The activity of the compound related to papaverine is 1.29. A 1 mg/kg. i.v. dose of the compound results in a 26% reduction in the arterial blood pressure of anaesthetized dogs.

EXAMPLE 11

To a solution of 4.6 g. of epichlorohydrin in 5.0 ml. of methanol 6.65 g. of 1,2,3,4-tetrahydro-isoquinoline are added dropwise, with stirring, under cooling at 0° to 10° C., for 2 hours. The reaction mixture is then stirred for one hour. In the next half an hour a solution of 11.8 g. of 3-(3,4-dimethoxybenzyl)-$\Delta^2$-1,2,4-oxadiazolin-5-one in 37 ml. of a 5% sodium hydroxide solution is added dropwise, and the mixture is stirred at room temperature for two hours. The oily product obtained is extracted with chloroform, the chloroform solution is washed with water, dried over sodium sulfate and the solvent is evaporated in vacuo. The residue is dissolved in isopropanol and is subsequently acidified with hydrochloric acid in absolute ethanol. 4.6 g. of 3-(3,4-dimethoxybenzyl)-4-[3-(1,2,3,4-tetrahydro-2-isoquinolyl)-2-hydroxypropyl]-$\Delta^2$-1,2,4-oxadiazolin-5-one hydrochloride are obtained, which has the same properties as the product of Example 10.

EXAMPLE 12

Following the procedure described in Example 2 but starting fom 3-(3,4-dimethoxybenzyl)-4-(3-chloro-2-hydroxypropyl)-$\Delta^2$-1,2,4-oxadiazolin-5one and 1-cyanomethyl-6,7-dimethoxy-1,2,3,4-tetrahydro-isoquinoline, 3-(3,4-dimethoxybenzyl)-4-[3-(1-cyanomethyl-6,7-dimethoxy-1,2,3,4-tetrahydro-2-isoquinolyl)-2-hydroxypropyl]-$\Delta^2$-1,2,4-oxadiazolin-5-one hydrochloride dihydrate is obtained, melting at 169° to 172° C. after recrystallization from 80% ethanol.

Analysis for $C_{27}H_{37}ClN_4O_9$: calculated: C=54.31%; H=6.25%; N=9.38%; Cl=5.94%; found: C=54.66%; H=6.26%; N=9.28%; Cl=6.05%.

EXAMPLE 13

To 1.6 g. of 3-(2,2-diphenylethyl)-4-(2,3-epoxypropyl)-$\Delta^2$-1,2,4-oxadiazolin-5-one 0.66 g. of 1,2,3,4-tetrahydro-isoquinoline and 25 ml. of absolute ethanol are added and the reaction mixture is refluxed for one hour. The solvent is evaporated in vacuo, and the residue is dissolved in isopropanol. Upon introducing hydrogen chloride 2.14 g. of 3-(2,2-diphenylethyl)-4-[3-(1,2,3,4-tetrahydro-2-isoquinolyl)-2-hydroxypropyl]-$\Delta^2$-1,2,4-oxadiazolin-5-one hydrochloride are obtained, melting at 250° C.

Analysis for $C_{28}H_{30}ClN_3O_3$: calculated: N=8.54%; Cl=7.21%; found: N=8.37%; Cl=7.06%.

EXAMPLE 14

Following the procedure described in Example 2 but starting from 43.06 g. of 3-(2,2-diphenylethyl)-4-(3-chloro-2-hydroxypropyl)-$\Delta^2$-1,2,4-oxadiazolin-5-one and 15.98 g. of 1,2,3,4-tetrahydro-isoquinoline, 44.9 g. of 3-(2,2-diphenylethyl)-4-[3-(1,2,3,4-tetrahydro-2-isoquinolyl)-2-hydroxypropyl]-$\Delta^2$-1,2,4-oxadiazolin-5-one hydrochloride are obtained, having the same properties as the product of Example 13.

EXAMPLE 15

To a solution of 1.9 g. of epichlorohydrin in 5 ml. of methanol 2.66 g of 1,2,3,4-tetrahydro-isoquinoline are portionwise added, with stirring, under cooling at 0° to 10° C., in 2 hours. The reaction mixture is stirred for one hour. Thereafter 5.3 g. of 3-(2,2-diphenylethyl)-$\Delta^2$-1,2,4-oxadiazolin-5-one in 15 ml. of a 5% sodium hydroxide solution are added dropwise, in half an hour. The mixture is stirred at room temperature for two hours, the product is extracted with benzene, the benzene solution is washed with water, dried over sodium sulfate and the solvent is evaporated in vacuo. The residue is dissolved in 50 ml. of isopropanol, the solution is acidified with hydrochloric acid in ethanol. 3.9 g. of 3-(2,2-diphenylethyl)-4-[3-(1,2,3,4-tetrahydro-2-isoquinolyl)-2-hydroxypropyl]-$\Delta^2$-1,2,4-oxadiazolin-5-one hydrochloride are obtained, having the same properties as the product of Example 13.

EXAMPLE 16

Following the procedure described in Example 2, but starting from 3-(2,2-diphenylethyl)-4-(3-chloro-2-hydroxypropyl)-$\Delta^2$-1,2,4-oxadiazolin-5-one and 1-methyl-6,7-dimethoxy-1,2,3,4-tetrahydro-isoquinoline, 3-(2,2-diphenylethyl)-4-[3-(1-methyl-6,7-dimethoxy-1,2,3,4-tetrahydro-2-isoquinolyl)-2-hydroxypropyl]-$\Delta^2$-1,2,4-oxadiazolin-5-one hydrochloride is obtained, melting at 228° to 230° C. after recrystallization from absolute ethanol.

Analysis for $C_{31}H_{36}ClN_3O_5$: calculated: C=65.77%; H=6.41%; N=7.42%; Cl=6.26%; found: C=66.11%; H=6.37%; N=7.29%; Cl=6.28%.

EXAMPLE 17

Following the procedure described in Example 2 but starting from 3-(2,2-diphenylethyl)-4-(3-chloro-2-hydroxypropyl)-$\Delta^2$-1,2,4-oxadiazolin-5-one and 1-cyanomethyl-6,7-dimethoxy-1,2,3,4-tetrahydro-isoquinoline, 3-(2,2-diphenylethyl)-4-[3-(1-cyanomethyl-6,7-dimethoxy-1,2,3,4-tetrahydro-2-isoquinolyl)-2-hydroxypropyl]-$\Delta^2$-1,2,4-oxadiazolin-5-one is obtained, melting at 218° to 220° C. after recrystallization from acetonitrile.

Analysis for $C_{32}H_{34}N_4O_5$: calculated: C=69.29%; H=6.18%; N=10.10%; found: C=69.46%; H=6.21%; N=10.10%.

EXAMPLE 18

Following the procedure described in Example 2 but starting from 3-phenyl-4-(3-chloro-2-hydroxypropyl)-$\Delta^2$-1,2,4-oxadiazolin-5-one and 1,2,3,4-tetrahydro-papaverine, 3-phenyl-4-{3-[1-(3,4-dimethoxy-benzyl)-6,7-dimethoxy-1,2,3,4-tetrahydro-2-isoquinolyl]-2-hydroxypropyl}-$\Delta^2$-1,2,4-oxadiazolin-5-one is obtained. Upon boiling 5.62 g. of the base obtained with 1.16 g. of maleic acid in 25 ml. of absolute ethanol for half an hour, maleate salt precipitates. Melting point (after recrystallization from absolute ethanol) 136° to 140° C.

Analysis for $C_{35}H_{39}N_3O_{11}$(677.7): calculated: C=62.03%; H=5.80%; N=6.20%; found: C=62.27%; H=5.97%; N=5.96%.

EXAMPLE 19

Following the procedure described in Example 2 but starting from 3-(2-chlorophenyl)-4-(3-chloro-2-hydroxypropyl)-$\Delta^2$-1,2,4-oxadiazolin-5-one and 1,2,3,4-tetrahydro-isoquinoline, 3-(2-chlorophenyl)-4-[3-(1,2,3,4-tetrahydro-2-isoquinolyl)-2-hydroxypropyl]-$\Delta^2$-1,2,4-oxadiazolin-5-one hydrochloride is obtained, melting at 216° to 218° C. after recrystallization from 80% ethanol.

Analysis for $C_{20}H_{21}N_3O_3Cl_2$ (422.3): calculated: C=56.88%; H=5.01%; N=9.95%; Cl=16,79%; found: C=56.61%; H=4.98%; N=9.85%; Cl=16.83%.

EXAMPLE 20

Following the procedure described in Example 2 but starting from 3-(2-chlorophenyl)-4-(3-chloro-2-hydroxypropyl)-$\Delta^2$-1,2,4-oxadiazolin-5-one and 6,7-dimethoxy-1,2,3,4-tetrahydro-isoquinoline, 3-(2-chlorophenyl)-4-[3-(6,7-dimethoxy-1,2,3,4-tetrahydro-2-isoquinolyl)-2-hydroxypropyl]-$\Delta^2$-1,2,3,4-oxadiazolin-5-one hydrochloride is obtained, melting at 235° to 237° C., after recrystallization from 80% ethanol.

Analysis for $C_{22}H_{25}N_3O_5Cl_2$(482.4): calculated: C=54.78%; H=5.22%; N=8.71%; Cl=14.70%; found: C=54.54%; H=5.20%; N=8.65%; Cl=14.46%.

EXAMPLE 21

Into a solution of 8.67 g. of 3-(2-chlorophenyl)-4-(3-chloro-2-hydroxypropyl)-$\Delta^2$-1,2,4-oxadiazolin-5-one and 10.3 g. of 1,2,3,4-tetrahydro-papaverine in 150 ml. of hot absolute ethanol 10.8 ml. of a 10% sodium hydroxide solution are added dropwise, in one hour. The reaction mixture is boiled for an additional one hour, and is then evaporated. To the evaporation residue 50 ml of water are added. 3-(2-chlorophenyl)-4-{3-[1-(3,4-dimethoxybenzyl)-6,7-dimethoxy-1,2,3,4-tetrahydro-2-isoquinolyl]-2-hydroxypropyl}-$\Delta^2$-1,2,4-oxadiazolin-5-one is obtained, as a crystalline substance. The product is converted into its hydrochloride by adding hydrochloric acid in absolute alcohol into its methanolic solution. Melting point: 160° to 163° C. (after recrystallization from 80% ethanol).

Analysis for $C_{31}H_{35}N_3O_7Cl_2$ (632.5): calculated: C=58.86%; H=5.58%; N=6.64%; Cl=11.21%;

found: C=58.33%; H=5.82%; N=6.57%; Cl=11.24%.

EXAMPLE 22

Following the procedure described in Example 21 but starting from 3-(4-chlorophenyl)-4-(3-chloro-2-hydroxypropyl)-Δ$^2$-1,2,4-oxadiazolin-5-one and 1,2,3,4-tetrahydro-papaverine, 3-(4-chlorophenyl)-4-{3-[1(3,4-dimethoxybenzyl)-6,7-dimethoxy-1,2,3,4-tetrahydro-2-isoquinolyl]-2-hydroxypropyl}-Δ$^2$-1,2,4-oxadiazolin-5-one is obtained, melting at 146° C., after recrystallization from absolute ethanol.

Analysis for C$_{31}$H$_{34}$N$_3$O$_7$Cl (596.1): calculated: C=62.46%; H=5.75%; N=7.05%; Cl=5.95%; found: C=62.41%; H=5.64%; N=6.88%; Cl=5.99%.

EXAMPLE 23

Following the procedure described in Example 2 but starting from 3-(4-methylphenyl)-4-(3-chloro-2-hydroxypropyl)-Δ$^2$-1,2,4-oxadiazolin-5-one and 1,2,3,4-tetrahydro-isoquinoline, 3-(4-methylphenyl)-4-[3-(1,2,3,4-tetrahydro-2-isoquinolyl)-2-hydroxypropyl]-Δ$^2$-1,2,4-oxadiazolin-5-one hydrochloride is obtained, melting at 208° to 210° C. after recrystallization from 96% ethanol.

Analysis for C$_{21}$H$_{24}$N$_3$O$_3$Cl (401.9): calculated: C=62.76%; H=6.02%; N=10.46%; Cl=8.82%; found: C=62.46%; H=5.91%; N=10.49%; Cl=8.78%.

EXAMPLE 24

Following the procedure described in Example 2 but starting from 3-benzyl-4-(3-chloro-2-hydroxypropyl)-Δ$^2$-1,2,4-oxadiazolin-2-one and 6,7-dimethoxy-1,2,3,4-tetrahydro-isoquinoline, 3-benzyl-4-[3-(6,7-dimethoxy-1,2,3,4-tetrahydro-2-isoquinolyl)-2-hydroxypropyl]-Δ$^2$-1,2,4-oxadiazolin-5-one hydrochloride is obtained, melting at 190° C., after recrystallization from absolute ethanol.

Analysis for C$_{23}$H$_{28}$N$_3$O$_5$Cl (461.9): calculated: C=59.80%; H=6.11%; N=9.10%; Cl=7.67%; found: C=59.50%; H=6.06%; N=8.73%; Cl=7.31%.

EXAMPLE 25

Following the procedure described in Example 21 but starting from 3-benzyl-4-(3-chloro-2-hydroxypropyl)-Δ$^2$-1,2,4-oxadiazolin-5-one and 1,2,3,4-tetrahydro-papaverine, 3-benzyl-4-{3-[1-(3,4-dimethoxybenzyl)-6,7-dimethoxy-1,2,3,4-tetrahydro-2-isoquinolyl]-2-hydroxypropyl}-Δ$^2$-1,2,4-oxadiazolin-5-one hydrochloride is obtained, melting at 215° C., after recrystallization from methanol.

Analysis for C$_{32}$H$_{38}$N$_3$O$_7$Cl (612.1): calculated: C=62.79%; H=6.26%; N=6.86%; Cl=5.79%; found: C=63.01%; H=5.91%; N=7.07%; Cl=5.97%.

EXAMPLE 26

Following the procedure described in Example 2 but starting from 3-(3,4-dimethoxybenzyl)-4-(3-chloro-2-hydroxypropyl)-Δ$^2$-1,2,4-oxadiazolin-5-one and 6,7-dimethoxy-1,2,3,4-tetrahydro-isoquinoline, 3-(3,4-dimethoxybenzyl)-4-[3-(6,7-dimethoxy-1,2,3,4-tetrahydro-2-isoquinolyl)-2-hydroxypropyl]-Δ$^2$-1,2,4-oxadiazolin-5-one hydrochloride is obtained, melting at 172° C. after recrystallization from absolute ethanol.

Analysis for C$_{25}$H$_{32}$N$_3$O$_7$Cl (521.98): calculated: C=57.52%; H=6.18%; N=8.05%; Cl=6.79%; found: C=57.68%; H=6,0%; N=8.02%; Cl=6.76%.

EXAMPLE 27

Following the procedure described in Example 21 but starting from 3-(3,4-dimethoxybenzyl)-4-(3-chloro-2-hydroxypropyl)-Δ$^2$-1,2,4-oxadiazolin-5-one and 1,2,3,4-tetrahydro-papaverine, 3-(3,4-dimethoxy-benzyl)-4-{3-[1-(3,4-dimethoxybenzyl)-6,7-dimethoxy-1,2,3,4-tetrahydro-2-isoquinolyl]-2-hydroxypropyl}-Δ$^2$-1,2,4-oxadiazolin-5-one hydrochloride is obtained, melting at 205° C., after recrystallization from methanol.

Analysis for C$_{34}$H$_{42}$N$_3$O$_9$Cl (672.2): calculated: C=60.75%; H=6.30%; N=6.25%; Cl=5.28%; found: C=60.78%; H=6.38%; N=6.22%; Cl=5.15%.

EXAMPLE 28

Tablets containing 30 mg. of active ingredient

| | |
|---|---|
| 3-phenyl-4-{3-[1-(3,4-dimethoxybenzyl)-6,7-dimethoxy-1,2,3,4-tetrahydro-2-isoquinolyl]-2-hydroxypropyl}-Δ$^2$-1,2,4-oxadiazolin-5-one hydrochloride | 30 mg. |
| starch | 80 mg. |
| silica gel | 20 mg. |
| magnesium stearate | 3 mg. |

EXAMPLE 29

Capsules containing 30 mg. of active ingredient

| | |
|---|---|
| 3-phenyl-4-{3-[1-(3,4-dimethoxybenzyl)-6,7-dimethoxy-1,2,3,4-tetrahydro-2-isoquinolyl]-2-hydroxypropyl}-Δ$^2$-1,2,4-oxadiazolin-5-one hydrochloride | 30 mg. |
| milk sugar | 40 mg. |
| filler | 5 mg. |

We claim:

1. A compound of the formula (I)

$$R^1-(CH)_m-(CH_2)_n-\underset{\underset{N\diagdown \phantom{x} \diagup C=O}{\overset{\|}{N}}}{\overset{}{C}}-\underset{\overset{}{O}}{N}-CH_2-\underset{\overset{}{OH}}{CH}- \quad (I)$$

$$-CH_2-N\underset{R^4}{\diagup}\hspace{-1em}\bigg\langle\text{tetrahydroisoquinoline with }R^3, R^3\bigg\rangle$$

wherein

R$^1$ is hydrogen, phenyl, or phenyl substituted by one or two alkyl groups having 1 to 4 carbon atoms, halogens, alkoxy groups having 1 to 4 carbon atoms;

R$^2$ is phenyl or phenyl substituted by one or two alkyl groups having 1 to 4 carbon atoms, halogens, alkoxy groups having 1 to 4 carbon atoms;

R$^3$ is alkoxy having 1 to 4 carbon atoms or hydrogen;

R$^4$ is hydrogen, alkyl having 1 to 4 carbon atoms unsubstituted or substituted by a cyano group or 3,4-dimethoxy-benzyl; m and n are each 0,1 or 2; or a pharmaceutically acceptable acid addition salt thereof.

2. 3-Phenyl-4-[3-(6,7-dimethoxy-1,2,3,4-tetrahydro-2-isoquinolyl)-2-hydroxypropyl]-Δ$^2$-1,2,4-oxadiazolin-5-one or a pharmaceutically acceptable acid addition salt thereof as defined in claim 1.

3. 3-(3,4-dimethoxybenzyl)-4-[3-(1,2,3,4-tetrahydro-2-isoquinolyl)-3-hydroypropyl]-Δ$^2$-1,2,4-oxadiazolin-5-one or a pharmaceutically acceptable acid addition salt thereof as defined in claim 1.

* * * * *